(12) United States Patent
Rashbaum et al.

(10) Patent No.: US 7,842,088 B2
(45) Date of Patent: Nov. 30, 2010

(54) INTERVERTEBRAL DISC PROSTHESIS

(75) Inventors: Ralph Rashbaum, Plano, TX (US); Kee D. Kim, Davis, CA (US); Hyun Bae, Santa Monica, CA (US)

(73) Assignee: LDR Medical, Troyes (FR)

( * ) Notice: Subject to any disclaimer, the term of this patent is extended or adjusted under 35 U.S.C. 154(b) by 602 days.

(21) Appl. No.: 11/341,007

(22) Filed: Jan. 27, 2006

(65) Prior Publication Data

US 2007/0073404 A1    Mar. 29, 2007

(30) Foreign Application Priority Data

Sep. 23, 2005    (FR)    .................................. 05 09740

(51) Int. Cl.
*A61F 2/44*    (2006.01)
(52) U.S. Cl. .................. 623/17.15; 623/17.14
(58) Field of Classification Search .... 623/17.11–17.16
See application file for complete search history.

(56) References Cited

U.S. PATENT DOCUMENTS

| | | |
|---|---|---|
| 566,360 A | 8/1896 | White |
| 1,436,573 A | 11/1922 | Choppinet et al. |
| 2,836,442 A | 5/1956 | Moskovitz |
| 3,325,197 A | 6/1967 | Wehner |
| 3,486,505 A | 12/1969 | Morrison |
| 3,857,642 A | 12/1974 | Miller |
| 3,958,278 A | 5/1976 | Lee et al. |
| 4,074,542 A | 2/1978 | Hankosky et al. |
| 4,085,466 A | 4/1978 | Goodfellow et al. |
| 4,309,777 A | 1/1982 | Patil |

(Continued)

FOREIGN PATENT DOCUMENTS

DE    2263842 A    7/1974

(Continued)

OTHER PUBLICATIONS

A biolological basis for instantaneous centres of rotation of the vertebral column, N. Bouduk, B. Amevo, M. Pearcy, Proc Insititution Mechanical Engineers, Jun. 16, 1995, pp. 177-183.

(Continued)

*Primary Examiner*—Todd E Manahan
*Assistant Examiner*—Ellen C. Hammond
(74) *Attorney, Agent, or Firm*—Civins Denko Coburn & Lauff LLP

(57) ABSTRACT

The invention relates to an intervertebral disc prosthesis comprising at least two plates, namely first and second plates, articulated about each other by means of a curved surface, namely articulation, of at least one of the plates, each of the plates comprising a surface known as a contact surface, intended to be in contact with a vertebral plate of one of the vertebrae between which the prosthesis is intended to be inserted, this contact surface for each of the plates comprising a geometrical centre at equal distance from at least two diametrically opposite points located on the periphery of the plate, in which the geometric centres of the plates are not vertically aligned, this off-setting of the geometrical centres of the plates engendering an off-setting of the edges of the plates in at least one direction perpendicular to the vertical axis of the spinal column.

24 Claims, 4 Drawing Sheets

U.S. PATENT DOCUMENTS

| | | |
|---|---|---|
| 4,349,921 A | 9/1982 | Kuntz |
| 4,655,778 A | 4/1987 | Koeneman |
| 4,714,469 A | 12/1987 | Kenna |
| 4,756,711 A | 7/1988 | Mai et al. |
| 4,759,766 A | 7/1988 | Buettner-Janz et al. |
| 4,759,769 A | 7/1988 | Hedman et al. |
| 4,787,908 A | 11/1988 | Wyss et al. |
| 4,863,476 A | 9/1989 | Sheppard |
| 4,874,389 A | 10/1989 | Downey |
| 4,892,545 A | 1/1990 | Day et al. |
| 4,911,718 A | 3/1990 | Lee et al. |
| 4,932,975 A | 6/1990 | Main |
| 4,946,378 A | 8/1990 | Hirayama et al. |
| 4,955,908 A | 9/1990 | Frey et al. |
| 4,955,916 A | 9/1990 | Carignan et al. |
| 4,997,432 A | 3/1991 | Keller |
| 5,002,576 A | 3/1991 | Fuhrmann et al. |
| 5,041,139 A | 8/1991 | Branemark |
| 5,071,437 A | 12/1991 | Steffee |
| 5,122,130 A | 6/1992 | Keller |
| 5,123,926 A | 6/1992 | Pisharodi |
| 5,171,281 A | 12/1992 | Parsons et al. |
| 5,192,327 A | 3/1993 | Brantigan |
| 5,197,986 A | 3/1993 | Mikhail |
| 5,246,458 A | 9/1993 | Graham |
| 5,258,031 A | 11/1993 | Salib et al. |
| 5,290,312 A | 3/1994 | Kojimoto et al. |
| 5,306,309 A | 4/1994 | Wagner et al. |
| 5,314,477 A | 5/1994 | Marney |
| 5,358,526 A | 10/1994 | Tornier |
| 5,370,697 A | 12/1994 | Baumgartner |
| 5,397,364 A | 3/1995 | Kozak et al. |
| 5,401,269 A | 3/1995 | Buettner-Janz et al. |
| 5,425,773 A | 6/1995 | Boyd et al. |
| 5,507,816 A | 4/1996 | Bullivant |
| 5,534,029 A | 7/1996 | Shima |
| 5,534,030 A | 7/1996 | Navarro et al. |
| 5,545,229 A | 8/1996 | Parsons et al. |
| 5,556,431 A | 9/1996 | Buettner-Janz et al. |
| 5,562,738 A | 10/1996 | Boyd et al. |
| 5,571,109 A | 11/1996 | Bertagnoli |
| 5,609,636 A | 3/1997 | Kohrs et al. |
| 5,645,596 A | 7/1997 | Kim |
| 5,674,294 A | 10/1997 | Bainville et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,702,472 A | 12/1997 | Huebner |
| 5,722,977 A | 3/1998 | Wilhelmy |
| 5,741,253 A | 4/1998 | Michelson |
| 5,766,252 A | 6/1998 | Henry et al. |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |
| 5,824,094 A | 10/1998 | Serhan et al. |
| 5,827,328 A | 10/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,063,088 A | 5/2000 | Winslow |
| 6,063,121 A | 5/2000 | Xavier et al. |
| 6,080,158 A | 6/2000 | Lin |
| 6,093,205 A | 7/2000 | McLeod et al. |
| 6,096,038 A | 8/2000 | Michelson |
| 6,096,080 A | 8/2000 | Nicholson et al. |
| 6,113,637 A | 9/2000 | Gill et al. |
| 6,113,638 A | 9/2000 | Williams et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 | 1/2001 | Zientek |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |
| 6,270,498 B1 | 8/2001 | Michelson |
| 6,277,149 B1 | 8/2001 | Boyle et al. |
| 6,283,998 B1 | 9/2001 | Eaton |
| 6,296,664 B1 | 10/2001 | Middleton |
| 6,306,170 B2 | 10/2001 | Ray |
| 6,315,797 B1 | 11/2001 | Middleton |
| 6,319,257 B1 | 11/2001 | Carignan et al. |
| 6,344,057 B1 | 2/2002 | Rabbe et al. |
| 6,364,880 B1 | 4/2002 | Michelson |
| 6,368,350 B1 * | 4/2002 | Erickson et al. .......... 623/17.14 |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,704 B1 | 7/2002 | Ferree |
| 6,419,706 B1 | 7/2002 | Graf |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,234 B1 | 11/2002 | Weber et al. |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,572,653 B1 | 6/2003 | Simonson |
| 6,579,291 B1 | 6/2003 | Keith et al. |
| 6,579,320 B1 | 6/2003 | Gauchet et al. |
| 6,582,468 B1 | 6/2003 | Gauchet et al. |
| 6,592,624 B1 | 7/2003 | Fraser et al. |
| 6,599,320 B1 | 7/2003 | Kuslich et al. |

| | | |
|---|---|---|
| 6,607,558 B2 | 8/2003 | Kuras |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |
| 6,616,671 B2 | 9/2003 | Landry et al. |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,652,533 B2 | 11/2003 | O'Neil |
| 6,652,586 B2 | 11/2003 | Hunter et al. |
| 6,656,224 B2 | 12/2003 | Middleton |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,915 B1 | 1/2004 | Cauthen |
| 6,682,562 B2 | 1/2004 | Viart et al. |
| 6,695,851 B2 | 2/2004 | Zdeblick et al. |
| 6,695,882 B2 | 2/2004 | Bianchi et al. |
| 6,706,068 B2 | 3/2004 | Ferree |
| 6,709,439 B2 | 3/2004 | Rogers et al. |
| 6,719,794 B2 | 4/2004 | Gerber et al. |
| 6,723,127 B2 | 4/2004 | Ralph et al. |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisemann et al. |
| 6,749,635 B1 | 6/2004 | Bryan |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,793,678 B2 | 9/2004 | Hawkins |
| 6,800,093 B2 | 10/2004 | Nicholson et al. |
| 6,814,737 B2 | 11/2004 | Cauthen |
| 6,824,565 B2 | 11/2004 | Muhanna et al. |
| 6,899,735 B2 | 5/2005 | Coates et al. |
| 6,936,071 B1 | 8/2005 | Marnay et al. |
| 6,964,686 B2 | 11/2005 | Gordon |
| 6,966,929 B2 | 11/2005 | Mitchell |
| 6,984,245 B2 | 1/2006 | McGahan et al. |
| 6,986,789 B2 | 1/2006 | Schultz et al. |
| 6,994,727 B2 | 2/2006 | Khandkar et al. |
| 7,001,432 B2 | 2/2006 | Keller et al. |
| 7,011,684 B2 | 3/2006 | Eckman |
| 7,025,787 B2 | 4/2006 | Bryan et al. |
| 7,056,344 B2 | 6/2006 | Huppert et al. |
| 7,060,097 B2 | 6/2006 | Fraser et al. |
| 7,060,099 B2 | 6/2006 | Carli et al. |
| 7,105,023 B2 | 9/2006 | Eckman |
| 7,105,024 B2 | 9/2006 | Richelsoph |
| 7,118,580 B1 | 10/2006 | Beyersdorff et al. |
| 7,153,325 B2 | 12/2006 | Kim et al. |
| 7,169,153 B2 | 1/2007 | Keller |
| 7,175,662 B2 | 2/2007 | Link et al. |
| 7,198,644 B2 | 4/2007 | Schultz et al. |
| 7,204,851 B2 | 4/2007 | Trieu et al. |
| 7,204,852 B2* | 4/2007 | Marnay et al. ............ 623/17.16 |
| 7,291,170 B2 | 11/2007 | Huppert |
| 2001/0020185 A1 | 9/2001 | Ray |
| 2002/0087212 A1 | 7/2002 | James et al. |
| 2002/0143343 A1 | 10/2002 | Castro |
| 2003/0028249 A1 | 2/2003 | Baccelli et al. |
| 2003/0055503 A1 | 3/2003 | O'Neil |
| 2003/0093156 A1 | 5/2003 | Metzger |
| 2003/0109928 A1 | 6/2003 | Pasquet et al. |
| 2003/0149438 A1 | 8/2003 | Nichols et al. |
| 2003/0171814 A1 | 9/2003 | Muhanna et al. |
| 2003/0187506 A1 | 10/2003 | Ross et al. |
| 2003/0220691 A1 | 11/2003 | Songer et al. |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010316 A1 | 1/2004 | William et al. |
| 2004/0030387 A1 | 2/2004 | Landry et al. |
| 2004/0034423 A1 | 2/2004 | Lyons et al. |
| 2004/0073309 A1 | 4/2004 | Bianchi et al. |
| 2004/0073311 A1 | 4/2004 | Ferree |
| 2004/0093082 A1 | 5/2004 | Ferree |
| 2004/0093083 A1 | 5/2004 | Branch et al. |
| 2004/0102846 A1 | 5/2004 | Keller et al. |
| 2004/0111160 A1 | 6/2004 | Evans et al. |
| 2004/0117022 A1 | 6/2004 | Marney et al. |
| 2004/0133278 A1 | 7/2004 | Marino et al. |
| 2004/0133281 A1 | 7/2004 | Khandkar et al. |
| 2004/0143332 A1* | 7/2004 | Krueger et al. ............ 623/17.14 |
| 2004/0148029 A1 | 7/2004 | Bianchi et al. |
| 2004/0153157 A1* | 8/2004 | Keller .................... 623/17.14 |
| 2004/0162617 A1 | 8/2004 | Zucherman et al. |
| 2004/0172020 A1 | 9/2004 | Beaurain et al. |
| 2004/0193273 A1 | 9/2004 | Huang |
| 2004/0199254 A1 | 10/2004 | Louis et al. |
| 2004/0220582 A1 | 11/2004 | Keller |
| 2004/0225295 A1 | 11/2004 | Zubok et al. |
| 2004/0225363 A1 | 11/2004 | Richelsoph |
| 2004/0225364 A1 | 11/2004 | Richelsoph |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2005/0010215 A1 | 1/2005 | Delecrin et al. |
| 2005/0015094 A1 | 1/2005 | Keller |
| 2005/0021042 A1 | 1/2005 | Marnay et al. |
| 2005/0027359 A1 | 2/2005 | Mashburn |
| 2005/0027363 A1 | 2/2005 | Gordon |
| 2005/0033305 A1 | 2/2005 | Schultz |
| 2005/0033437 A1 | 2/2005 | Bao et al. |
| 2005/0033438 A1 | 2/2005 | Schultz |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0060034 A1 | 3/2005 | Berry et al. |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marney et al. |
| 2005/0107788 A1 | 5/2005 | Beaurain et al. |
| 2005/0113926 A1 | 5/2005 | Zucherman et al. |
| 2005/0119665 A1 | 6/2005 | Keller |
| 2005/0131542 A1 | 6/2005 | Benzel et al. |
| 2005/0143824 A1 | 6/2005 | Richelsoph et al. |
| 2005/0149189 A1 | 7/2005 | Mokhtar et al. |
| 2005/0159818 A1 | 7/2005 | Blain |
| 2005/0165408 A1 | 7/2005 | Puno et al. |
| 2005/0165485 A1 | 7/2005 | Trieu |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1 | 9/2005 | Hovorka et al. |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0283242 A1 | 12/2005 | Zucherman et al. |

| | | | |
|---|---|---|---|
| 2006/0015183 A1 | 1/2006 | Gilbert et al. | |
| 2006/0020341 A1 | 1/2006 | Schneid et al. | |
| 2006/0030860 A1 | 2/2006 | Peterman | |
| 2006/0036326 A1 | 2/2006 | Baumgartner et al. | |
| 2006/0041313 A1 | 2/2006 | Allard et al. | |
| 2006/0041314 A1 | 2/2006 | Millard | |
| 2006/0069437 A1 | 3/2006 | Weber | |
| 2006/0069441 A1 | 3/2006 | Zucherman et al. | |
| 2006/0111783 A1 | 5/2006 | Aflatoon et al. | |
| 2006/0116768 A1 | 6/2006 | Krueger et al. | |
| 2006/0116769 A1 | 6/2006 | Marnay et al. | |
| 2006/0122703 A1 | 6/2006 | Aebi et al. | |
| 2006/0136063 A1 | 6/2006 | Zeegers | |
| 2006/0142863 A1 | 6/2006 | Fraser et al. | |
| 2006/0149273 A1 | 7/2006 | Ross et al. | |
| 2006/0149371 A1 | 7/2006 | Marik et al. | |
| 2006/0149378 A1 | 7/2006 | Chase et al. | |
| 2006/0155377 A1 * | 7/2006 | Beaurain et al. | 623/17.15 |
| 2006/0155378 A1 | 7/2006 | Eckman | |
| 2006/0173544 A1 | 8/2006 | Gau | |
| 2006/0178746 A1 | 8/2006 | Bartish, Jr. et al. | |
| 2006/0190082 A1 | 8/2006 | Keller et al. | |
| 2006/0200241 A1 | 9/2006 | Rothman et al. | |
| 2006/0200242 A1 | 9/2006 | Rothman et al. | |
| 2006/0200243 A1 | 9/2006 | Rothman et al. | |
| 2006/0212123 A1 | 9/2006 | Lechmann et al. | |
| 2006/0235520 A1 | 10/2006 | Pannu | |
| 2006/0235526 A1 | 10/2006 | Lemaire | |
| 2006/0259143 A1 | 11/2006 | Navarro et al. | |
| 2006/0265072 A1 | 11/2006 | Richelsoph | |
| 2006/0282074 A1 | 12/2006 | Renaud et al. | |
| 2006/0287728 A1 | 12/2006 | Mokhtar et al. | |
| 2007/0010887 A1 | 1/2007 | Williams et al. | |
| 2007/0016217 A1 | 1/2007 | Dinville | |
| 2007/0016299 A1 | 1/2007 | Eckman | |
| 2007/0055378 A1 | 3/2007 | Ankney et al. | |
| 2007/0073403 A1 | 3/2007 | Lombardo et al. | |
| 2007/0073404 A1 | 3/2007 | Rashbaum et al. | |
| 2007/0088362 A1 | 4/2007 | Bonutti et al. | |
| 2007/0100454 A1 | 5/2007 | Burgess et al. | |
| 2007/0100455 A1 | 5/2007 | Parsons | |
| 2007/0100456 A1 | 5/2007 | Dooris et al. | |
| 2007/0149974 A1 | 6/2007 | Mangione | |
| 2007/0162130 A1 | 7/2007 | Rashbaum et al. | |
| 2007/0270951 A1 | 11/2007 | Davis et al. | |
| 2009/0228108 A1 * | 9/2009 | Keller | 623/17.16 |

FOREIGN PATENT DOCUMENTS

| | | |
|---|---|---|
| DE | 2804936 | 8/1979 |
| DE | 3023353 A | 4/1981 |
| DE | 8912648 U | 11/1990 |
| DE | 20310432 U | 9/2003 |
| DE | 20310433 U | 9/2003 |
| DE | 102004027985 | 7/2005 |
| EP | 42271 | 12/1981 |
| EP | 176728 | 4/1986 |
| EP | 0298235 A | 1/1989 |
| EP | 0317972 A | 5/1989 |
| EP | 0333990 A | 9/1989 |
| EP | 0356112 | 2/1990 |
| EP | 0512529 A | 11/1992 |
| EP | 0560141 A | 9/1993 |
| EP | 0566810 A1 | 10/1993 |
| EP | 0566810 B1 | 5/1996 |
| EP | 0738504 | 10/1996 |
| EP | 0747025 A1 | 12/1996 |
| EP | 0852934 | 7/1998 |
| EP | 0903126 | 3/1999 |
| EP | 0955021 A | 11/1999 |
| EP | 0978258 | 2/2000 |
| EP | 1250898 A1 * | 10/2002 |
| EP | 1344506 | 9/2003 |
| EP | 1344508 | 9/2003 |
| EP | 1374808 | 12/2005 |
| FR | 2124815 A | 9/1972 |
| FR | 2372622 | 6/1978 |
| FR | 2632516 A | 12/1989 |
| FR | 2659226 A | 9/1991 |
| FR | 2716619 | 9/1995 |
| FR | 2718635 A1 | 3/1996 |
| FR | 2723841 | 3/1996 |
| FR | 2724108 A | 3/1996 |
| FR | 2730159 A1 | 8/1996 |
| FR | 2737656 A | 2/1997 |
| FR | 2787019 | 12/1998 |
| FR | 2787021 A | 6/2000 |
| FR | 2824261 | 11/2002 |
| FR | 2831796 | 5/2003 |
| FR | 2843293 | 2/2004 |
| FR | 2846550 | 5/2004 |
| FR | 2865629 | 8/2005 |
| FR | 2865630 A1 | 8/2005 |
| FR | 2869528 | 11/2005 |
| JP | 2261446 | 10/1990 |
| WO | WO9011740 A | 10/1990 |
| WO | WO9107931 | 6/1991 |
| WO | WO9113598 A | 9/1991 |
| WO | WO9301771 A | 2/1993 |
| WO | WO9404100 | 3/1994 |
| WO | WO9909914 | 3/1999 |
| WO | WO9953871 | 10/1999 |
| WO | WO9956675 A | 11/1999 |
| WO | WO9965412 | 12/1999 |
| WO | WO9966864 | 12/1999 |
| WO | WO0053127 A | 9/2000 |
| WO | WO0074606 A | 12/2000 |
| WO | WO0101893 A | 1/2001 |
| WO | WO0119295 A | 3/2001 |
| WO | WO0141680 | 6/2001 |
| WO | WO0162191 | 8/2001 |
| WO | WO02071960 | 9/2002 |
| WO | WO02089701 A2 | 11/2002 |
| WO | WO03015646 | 2/2003 |
| WO | WO03039400 A2 | 5/2003 |
| WO | WO03045262 | 6/2003 |
| WO | WO03059212 A | 7/2003 |
| WO | WO03075803 | 9/2003 |
| WO | WO03075804 A | 9/2003 |
| WO | WO2004041129 A1 | 5/2004 |
| WO | WO2004041131 | 5/2004 |
| WO | WO2005046534 | 5/2005 |
| WO | WO2005074839 | 8/2005 |
| WO | WO2005104996 | 11/2005 |
| WO | WO2005117728 | 12/2005 |
| WO | WO2006136760 | 12/2006 |

OTHER PUBLICATIONS

A Multicenter Retrospective Study of the Clinical Results of the Link SB Charite Intervertebral Prosthesis, S. L. Griffith, PhD, A. P. Shelokov, MD, K. Buttner-Janz, MD, Jean-Phillipe LeMaire, MD and W. S. Zeegers, MD, Spine, vol. 19, No. 16, pp. 1842-1849, Mar. 21, 1994.

A New Technique for the Three-Dimensional Study of the Spine in Vitro and In Vivo by Using a Motion-Analysis System, X. Liu, G. Fabry, K. Labey, L. Van Den Berghe, R. Van Audekercke, G. Molenaers, P. Moens, Journal of Spinal Disorders, vol. 10, No. 4, pp. 329-338, Jan. 30, 1997.

Alternatives to Spinal Fusion, J. P. Kostuik, Spinal Fusion, vol. 29, No. 4, Oct. 1998, pp. 701-415.

Centrode Patterns and Segmental Instability in Degenerative Disc Disease, S.D. Gertzban, MD, FRCSC, J. Seligman, MD, R. Holtby, MD, K.H. Chan, MD, A. Kapasouri, BSc, M. Tile, MD, BSc, (MED), FRCS ©, and B. Cruickshank, MD, FRCPath, Spine, vol. 10., No. 3, pp. 257-261, Jan. 21, 1984.

Clinical Biomechanics of the Spine, A. A. White III, M. M. Panjabi, pp. 128-130, 2nd Edition, J.B. Lippincott Co., 1990.
Computer Analysis of Spinal Segment Motion in Degenerative Disc Disease With and Without Axial Loading, J.V. Seligman, S.D. Gertzbein, M. Tile, A., Kapasouri, Spine, vol. 9., No. 6, pp. 566-573, Dec. 31, 1983.
FR 2 718 635 Preliminary Search Report, National Institute of Industrial Property (France), Jan. 16, 1995.
FR 2 730 159 Preliminary Search Report, National Institute of Industrial Property (France), Sep. 29, 1995.
FR 2 824 261 Preliminary Search Report, National Institute of Industrial Property (France), Feb. 25, 2002.
FR 2 831 796 Preliminary Search Report, National Institute of Industrial Property (France), Aug. 2, 2002.
FR 2 846 550 Preliminary Search Report, National Institute of Industrial Property (France), Jul. 10, 2003.
FR 2 865 629 Preliminary Search Report, National Institute of Industrial Property (France), Sep. 14, 2004.
FR 2 865 630 Preliminary Search Report, National Institute of Industrial Property (France), Jan. 12, 2005.
FR 2 869 528 Preliminary Search Report, National Institute of Industrial Property (France), Dec. 13, 2004.
Instantaneous Axis of Rotation as a Function of the Three Columns of the Spine, T. R. Haher, MD, M. O'Brien, MD, W. T. Felmly, MD, D. Welin, MD, G. Perrier, MD., J. Choueka, MD, V. Devlin, MD, A. Vassiliou, ME, and G. Chow, MS, Spine, vol. 17, No. 6, pp. S149-S154, Jan. 9, 1992.
Instantantaneous Axis of Rotation of the Lumbar Intervertebral Joints, M. J. Pearcy, H. Bogduk, Spine, vol. 13, No. 9, pp. 1033-1041, Nov. 15, 1987.
Mobidisc (website) 1 page, www.ldrmedical.fr/mobidisc.htm, Sep. 19, 2004.
Motion Characteristics of the Normal Lumbar Spine in Young Adults: Instantaneous of Axis of Rotation and Vertebral Center Motion Analysis, T. Yoshioka, H. Tsuji, N. Hirano and S. Sainoh, Journal of Spinal Disorders, vol. 3, No. 2, pp. 103-113, 1990.
PCT/IB02/02998 International Search Report, EPO, Sep. 16, 2003.
PCT/IB02/04642 International Search Report, EPO, Jul. 2, 2003.
PCT/IB05/00280 International Search Report, EPO, Jun. 24, 2005.
PCT/IB05/01151 International Search Report, EPO, Sep. 12, 2005.
PCT/IB03/04872 International Search Report, EPO, Mar. 3, 2004.
PCT/IB02/02998 International Preliminary Examination Report, EPO, Dec. 22, 2003.
PCT/IB02/04642 International Preliminary Examination Report, EPO, Apr. 1, 2004.
PCT/IB03/04872 International Preliminary Examination Report, EPO, Mar. 1, 2005.
Relocation of the Bending Axis During Flexion-Extension of Lumbar Intervertebral Discs and its Implications for Prolapse, J.A. Klein and D.W.L. Hukins,Spine, vol. 8, No. 6, pp. 659-664, Nov. 18, 1982.
The Effect of the Three Columns of the Spine on the Instantaneous Axis of Rotation in Flexion and Extension, T. R. Haher, M. Bergman, M. O'Brien, W. T. Felmly, J. Choueka, D. Welin, G. Chow, A. Vassiliou, Spine, vol. 16, No. 8, pp. S312-S318, Apr. 16, 1991.
USPTO OA of Feb. 6, 2007 in U.S. Appl. No. 11/108,276.
USPTO OA of Oct. 16, 2007 in U.S. Appl. No. 11/109,276.
USPTO OA of Jul. 24, 2008 in U.S. Appl. No. 11/109,276.
USPTO OA of Feb. 13, 2009 in U.S. Appl. No. 11/109,276.
Applicant's Reply to USPTO OA of Feb. 6, 2007 in U.S. Appl. No. 11/109,276.
Applicant's Reply to USPTO OA of Oct. 16, 2007 in U.S. Appl. No. 11/109,276.
Applicant's Reply to USPTO OA of Jul. 24, 2008 in U.S. Appl. No. 11/109,276.
Applicant's Response to USPTO OA of Feb. 13, 2009 in U.S. Appl. No. 11/109,276.
USPTO OA of Apr. 18, 2007 in U.S. Appl. No. 10/533,846.
Applicant's Response to USPTO OA of Apr. 18, 2007 in U.S. Appl. No. 10/533,846.
USPTO OA of Dec. 26, 2007 in U.S. Appl. No. 10/533,846.
Applicant's Response to USPTO OA of Dec. 26, 2007 in U.S. Appl. No. 10/533,846.
USPTO OA of Oct. 15, 2008 in U.S. Appl. No. 10/533,846.
Applicant's Response to USPTO OA of Oct. 15, 2008 in U.S. Appl. No. 10/533,846.
USPTO OA of Jan. 22, 2008 in U.S. Appl. No. 11/180,868.
Applicant's Response to USPTO OA of Jan. 22, 2008 in U.S. Appl. No. 11/180,868.
USPTO OA of Nov. 5, 2008 in U.S. Appl. No. 11/180,868.
Response to USPTO OA of Nov. 5, 2008 in U.S. Appl. No. 11/180,868.
USPTO OA of Mar. 20, 2009 in U.S. Appl. No. 11/676,237.
USPTO OA of Feb. 18, 2009 in U.S. Appl. No. 11/632,253.
Applicant's Response to USPTO OA of Feb. 18, 2009 in U.S. Appl. No. 11/632,253.

* cited by examiner

INTERVERTEBRAL DISC PROSTHESIS

CROSS REFERENCE TO RELATED APPLICATIONS

This application claims priority from Application No. FR 0509740 filed in France on Sep. 23, 2005, which in incorporated herein by reference for all purposes.

BACKGROUND

The invention relates to an intervertebral disc prosthesis, intended to be substituted for fibrocartilaginous discs providing the liaison between the vertebrae of the spinal column.

Different types of intervertebral disc prostheses are known in the prior art. Numerous prostheses, such as for example those described in the applications WO 02 089 701 and WO 2004/041129, are constituted of a lower plate and an upper plate creating a cage articulated about a central core. Other prostheses like those disclosed in the patent U.S. Pat. No. 5,676,701 and in the application WO 03/059212 A1, for example, only comprise a lower plate and an upper plate articulated about themselves by means of a surface of articulation. These articulated prostheses have the advantage of offering the patient bearing the prosthesis a freedom of movement, by allowing the plates to tilt and/or rotate in relation to each other. The prostheses comprising a central core, movable between the plates, have the added advantage of allowing a spontaneous positioning of the core in the ideal position for absorbing the constraints imposed on the prosthesis. In these prostheses known in the prior art, the anterior, posterior and lateral edges of a plate are located on the same vertical axis as the corresponding edge of the other plate. This shape of the prosthesis is normally due to the plates being of identical size and that their respective axes of articulation are joined (coaxially), so as to facilitate the movements of the patient and to allow the correction of possible positioning defects. However, these prostheses have the inconvenience of not being perfectly suited to the morphology of the spinal column. Indeed, the posterior edges of two adjacent vertebrae are often slightly off-set to each other. Thus, the prostheses known in the prior art are difficult to properly implant. Additionally, at rest, due to the natural off-setting of the vertebrae and the anchoring of the plates in the vertebrae, the different parts of the prosthesis are under constraint in an undesirable position as it restricts freedom of movement of these parts of the prosthesis. This inconvenience will be diminished through the use of a movable core between the plates, but the possible movements of the core will be restricted and its capacity to position itself so as to absorb the constraints imposed on the prosthesis will therefore be diminished.

In this context, it is beneficial to propose a prosthesis that allows a more efficiently fit to the profile of the spinal column and thus fully attain the goals it set by offering a surface of articulation.

SUMMARY

The purpose of the invention is to overcome some of the inconveniences of the prior art by proposing an intervertebral disc prosthesis at least comprising two plates each bearing at least an edge off-set in relation to the same edge of the other plate.

This goal is reached with an intervertebral disc prosthesis comprising at least two plates, namely first and second plates, articulated about each other by means of a curved surface, namely articulation, of at least one of the plates, allowing to pivot and/or tilt the plates in relation to each other, via rotation about, respectively, an axis substantially perpendicular to the plane of the plates and an axis substantially in the plane of the plates, each of the plates comprising a surface known as a contact surface, intended to be in contact with a vertebral plate of one of the vertebrae between which the prosthesis is intended to be implanted, this contact surface for each of the plates comprising a geometric centre at equal distance from at least two diametrically opposite points located on the periphery of the plate, characterised in that the geometric centres of the plates are not vertically aligned, this off-set of the geometrical centres of the plates engendering an off-set of the edges of the plates in at least one direction perpendicular to the vertical axis of the spinal column.

According to another feature, the second plate comprises a curved surface of articulation of which at least one part co-operates with a curved surface of articulation of the first plate for which it is complementary, in order to allow the articulation, by pivoting and/or tilting, of the plates in relation to each other, the prosthesis comprising a centre of articulation vertically aligned with the vertex of the curved surface of articulation of the second plate and corresponding to the mid-position of the centre of the curved surface of the first plate in relation to the second plate.

According to another feature, the curved surface of the first plate is concave and the curved surface of articulation of the second plate is convex.

According to another feature, the curved surface of the first plate is convex and the curved surface of articulation of the second plate is concave.

According to another feature, the prosthesis also comprises a core comprising a plane surface and a curved surface of articulation and in that only the first plate comprises a curved surface of articulation co-operating with at least one part of the curved surface of the core for which it is complementary, in order to allow the pivoting and/or tilting of the plates in relation to each other, the plane surface of the core co-operating with at least one part of a plane surface of the second plate in order to allow a translation and/or a rotation of the core in relation to the second plate in at least one direction perpendicular to the vertical axis of the spinal column, the second plate comprising means for co-operating complementary with means for co-operating of the core allowing to restrict or abolish at least this translation of the core in relation to the second plate, the prosthesis comprising a centre of articulation vertically aligned with the vertex of the curved surface of articulation of the core and corresponding to the mid-position of the core between the means for co-operating of the second plate and to the mid-position of the centre of the curved surface of the first plate in relation to the core.

According to another feature, the curved surface of the first plate is concave and the curved surface of the core is convex.

According to another feature, the curved surface of the first plate is convex and the curved surface of the core is concave.

According to another feature, the prostheses comprises a centre of articulation vertically aligned with the vertex of the curved surface of articulation, said centre of articulation being vertically aligned with the geometric centre of the first plate but off-set in relation to the geometric centre of the second plate in at least one direction perpendicular to the vertical axis of the spinal column, this off-setting of the geometric centres of the plates engendering an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate but in the opposite direction to that of its off-setting in relation to the geometric centre of the second plate, so that the vertical projection of the centre of articulation is located between the vertical projections of the geometric centres of the plates and that the off-setting of the geometric centres in relation to the centre of articulation cumulate and engender an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate, in the same direction as that of its off-setting in relation to the geometric centre of the second plate, but at a lesser distance so that these off-settings partially compensate each other and engender an off-setting of the edges of the plates between themselves in at least one direction perpendicular to the vertical axis of the spinal column.

According to another feature, the means for co-operating of the second plate are female means located in the vicinity of the edges of the second plate and co-operating with the male means of the core.

According to another feature, the dimensions of each male means for co-operating are slightly smaller than those of the female means for co-operating in order to allow a slight travel between the core and the second plate around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the means for co-operating of the second plate are the male means located in the vicinity of the edges of the second plate and co-operating with the female means of the core.

According to another feature, the dimensions of each male means for co-operating are slightly smaller than those of each female means for co-operating in order to allow as slight travel between the core and the second plate, around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the male means for co-operating of the core are two studs located on the two side edges of the core and the female means for co-operating of the second plate are four walls located, in pairs, on each of the two side edges of the second plate.

According to another feature, the female means for co-operating of the second plate comprise a section dish-shaped towards the centre of the plate and partly covering the male means for co-operating of the core in order to prevent the core from lifting.

According to another feature, the median planes representing the contact surfaces of the plates are substantially parallel or create an acute angle, the slope obtained by such an angle allowing to adapt the overall shape of the prosthesis to the anatomy of the spinal column or to possibly correct any slope defects of the vertebrae of the patient for whom the prosthesis is intended for.

According to another feature, the plates comprise, at least on their lower edge, at least a bevel facilitating the insertion of the prosthesis between the vertebrae.

According to another feature, the same plates can be assembled with cores of different thicknesses and/or dimensions and/or shapes.

According to another feature, the plates comprise mobile osseous anchorage means.

According to another feature, the osseous anchorage means and/or the plates comprise means for securing the binding of the osseous anchorage means on the plates.

According to another feature, the mobile osseous anchorage means of the plates consists in at least one plate equipped with notches oriented so as to prevent this notched plate from falling out once inserted in a vertebra, one end of the plate having an inward curving section and intended to be interlocked onto at least one edge of an opening located in the vicinity of the periphery of the plates.

According to another feature, the end of the notched plate, opposite the one with an inward curving section, comprises a bevel facilitating the insertion of the notched plate into the vertebrae.

According to another feature, the opening located in the vicinity of the periphery of the plates comprises a sloping section on which the notched plate leans when the curved section of the osseous anchorage means is interlocked onto the edge of this opening, this sloping section thus allowing to set the angle of the osseous anchorage means in relation to the plates and to guide them when being inserted into the opening.

According to another feature, the means for securing consist in flexible tabs oriented towards the curved section of the osseous anchorage means and intended to fold back against the edges of the plate when inserting the osseous anchorage means into the openings in the plates, then to spring back so as to lean against the limit stops located on the walls of the openings in the plates during the interlocking of the curved sections onto the edges of the openings in the plates, so as to prevent the osseous anchorage means from falling out.

According to another feature, the inward curving section of the notched plate of the mobile osseous anchorage means extends by means of a second plate also equipped with notches oriented so as to prevent the plate from falling out once inserted into the vertebra.

According to another feature, the mobile osseous anchorage means of the plates consist in at least a winglet equipped with notches oriented so as to prevent the winglet from falling out once inserted in a groove made in a vertebra, one end of the winglet having an inward curving section and intended to be interlocked on to at least one edge of an opening in the vicinity of the periphery of the plates.

According to another feature, the means for securing the winglet consist in at least one stud located on the lower surface of the winglet and intended to be interlocked into at least one hole in the contact surfaces of the plates, the stud and the hole being of complementary shape and size so as to secure the winglet in place on the plates.

BRIEF DESCRIPTION OF THE DRAWINGS

Other features and advantages of the invention will become clearer upon reading the following description, given in reference to the annexed figures, in which.

DETAILED DESCRIPTION OF THE EMBODIMENTS

Figure 1A:
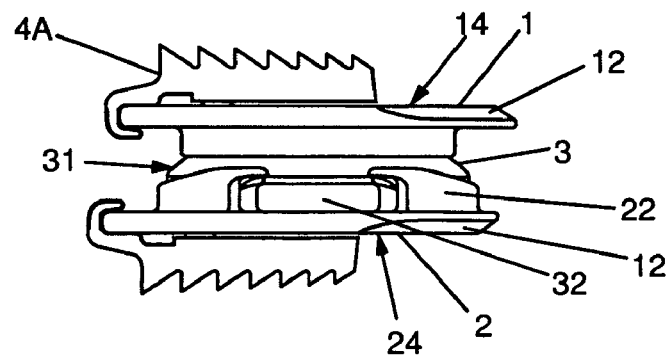
FIGS. 1A, 1B and 1C respectively represent a side view, a rear view with a cross section plane 1C-1C and a cross section along said plane 1C-1C, of an intervertebral disc prosthesis according to an embodiment of the invention, FIGS. 2A, 2B and 2C respectively represent a side view, a rear view with a cross section plane 2C-2C and a cross section along said plane 2C-2C, of an intervertebral disc prosthesis according to another embodiment of the invention, FIGS. 3A and 3B respectively represent a rear view with a cross section plane 3B-3B and a cross section along said plane 3B-3B, of an intervertebral disc prosthesis according to an embodiment of the invention and FIGS. 3C and 3D respectively represent a rear view with a cross section plane 3D-3D and a cross section along said plane 3D-3D, of an intervertebral disc prosthesis according to another embodiment of the invention, FIGS. 4A and 4B respectively represent a top view and a perspective view of an embodiment of the osseous anchorage means of an intervertebral disc prosthesis according to the invention, and FIGS. 4C and 4D respectively represent a top view and a side view of another embodiment of the osseous anchorage means of an intervertebral disc prosthesis according to the invention, FIGS. 5A, 5B and 5C respectively represent a perspective view, a top view and a side view of an intervertebral disc prosthesis according to different embodiments of the invention.

The invention relates to an intervertebral disc prosthesis comprising at least two plates (1, 2) off-set in relation to each other so as to more efficiently follow the anatomy of the spinal column. As explained in the preamble of this application, the vertebrae are generally slightly off-set to each other, so that their edges, for example posterior, are not vertically aligned. The prosthesis according to the invention is thus designed so that the edges of the plates (1, 2) are not vertically aligned and have a slight off-setting corresponding to an off-setting between the edges of the vertebrae between which the prosthesis is intended to be inserted. The off-setting of the vertebrae could have been accurately measured beforehand, in order to choose a prosthesis whose off-setting of the plates (1, 2) perfectly corresponds to the off-setting of the vertebrae.

The plates (1 and 2) of the prosthesis according to the invention each comprise a geometric centre (G1 and G2, respectively) which can be defined, generally speaking, by a point at equal distance from two diametrically opposite points located on the periphery of the plates (1, 2). Normally, the plates of the intervertebral disc prostheses have a relatively straightforward shape and their geometric centre can be of equal distance from all the points located on the periphery of the plates. Irrespective of the prosthesis, a geometric centre can be defined by a point or a surface located at equal distance from the edges of the plate. The geometric centres (G1, G2) of the plates (1, 2) of the prosthesis according to the invention are not vertically aligned but are off-set to each other in at least one direction, for example antero-posterior, perpendicular to the vertical axis of the spinal column. The two plates (1 and 2) of a single intervertebral disc prosthesis are usually substantially the same size and this off-set (D) of the geometric centres (G1, G2) of the plates engenders an off-set of the edges of the plates (1, 2). In the case of a prosthesis whose plates are not of the same size, it is envisaged to off-set the edges of the plates (1 and 2) and the geometric centres (G1, G2) will be even more off-set to each other.

In the different embodiments described below, the prosthesis comprises at least two plates (1 and 2), namely first (1) and second (2) plates, articulated about each other by means of a curved surface (11, 31), namely articulation, of at least one of the plates. This curved surface (11, 31) of articulation allows to pivot the plates (1, 2) about each other, via rotation about an axis substantially perpendicular to the plane of the plates and/or to tilt the plates (1, 2) about each other, via rotation about an axis substantially along the plane of the plates (1, 2). Each of the plates (1, 2) comprises a surface (14, 24) known as a contact surface, intended to be in contact with a vertebral plate of one of the vertebrae between which the prosthesis is intended to be inserted. The geometric centre will hereafter be defined in relation to this contact surface for the sake of ease but it must be understood that it is the vertical axis passing through the geometric centre which matters in the principle of the invention and that the exact position of the geometric centre on the width of the plates has no relevance. In the different embodiments described below, each of the plates (1, 2) therefore comprises a geometric centre (G1, G2) at equal distance from at least two diametrically opposite points located on the periphery of the plate (1, 2). The geometric centres (G1, G2) of the plates (1, 2) are not vertically aligned and this off-set (D) of the geometrical centres (G1, G2) of the plates engenders an off-set of the edges of the plates (1, 2) in at least one direction perpendicular to the vertical axis of the spinal column.

Figure 2A:
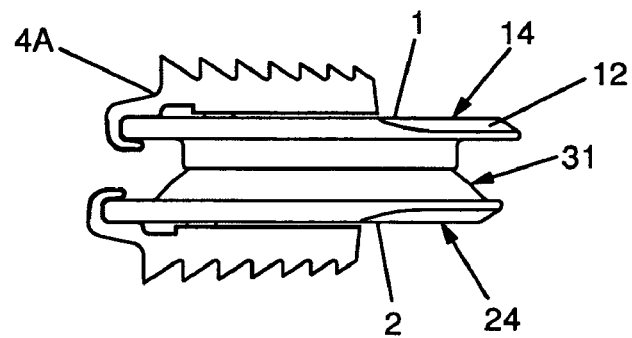
Figure 2B:
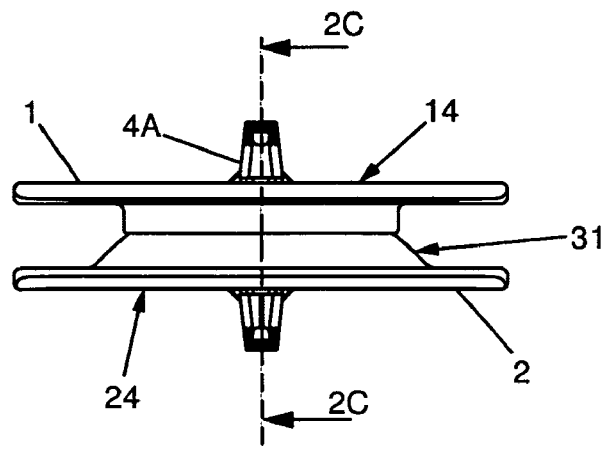
Figure 2C:
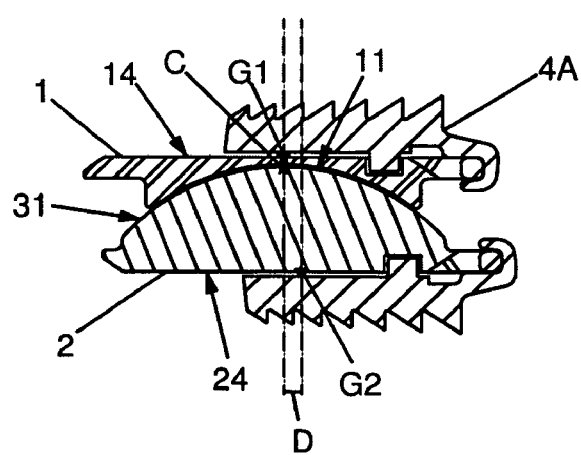
Figure 3A:
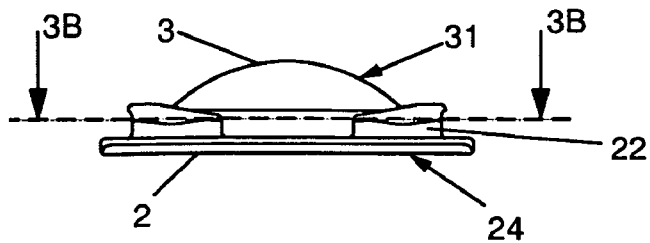
Figure 3B:
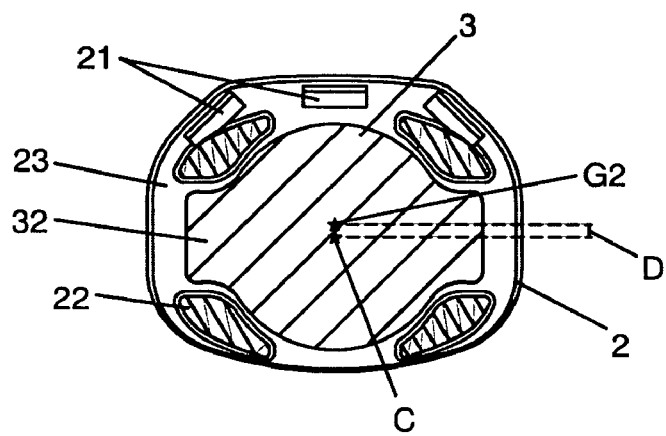
Figure 3C:
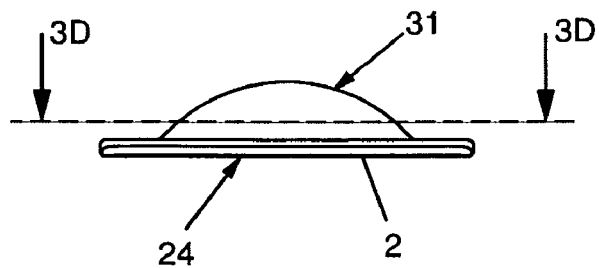
Figure 3D:
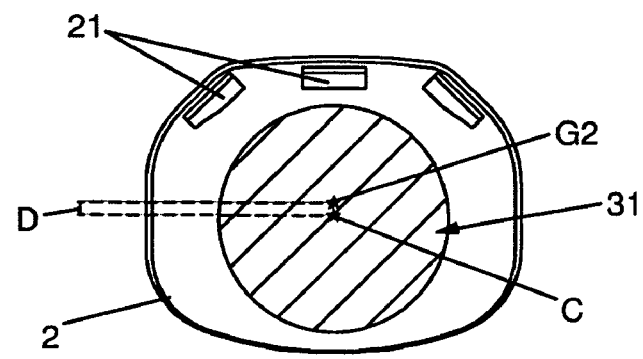
Figure 4A:
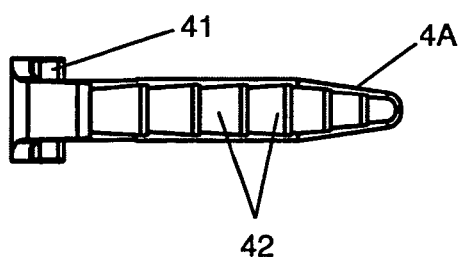
Figure 4B:
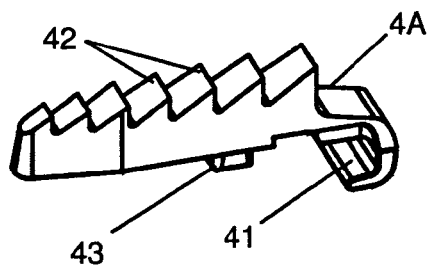
Figure 4C:
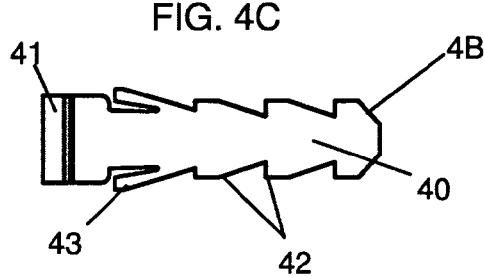
Figure 4D:
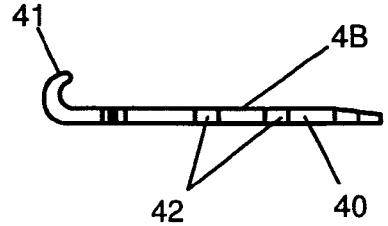

In the embodiment represented in FIGS. 2A, 2B, 2C, 3C and 3D, the prosthesis only comprises two elements: two plates (1, 2). In this case, the second plate (2) comprises a curved surface (31) of articulation of which at least one section co-operates with a curved surface (11) of articulation of the first plate (1) to which it is complementary. The co-operating of these curved surfaces (11, 31) of articulation allows to pivot and/or tilt the plates (1, 2) about each other. A centre (C) of articulation vertically aligned with the vertex of the curved surface (31) of articulation of the second plate (2) can be defined. This centre (C) of articulation corresponds to the mid-position of the centre of the curved surface (11) of the first plate (1) compared to the second plate (2). In the embodiment represented in the figures, the curved surface (11) of the first plate (1) is concave and the curved surface (31) of articulation of the second plate (2) is convex but it can be the case that the curved surface (11) of the first plate (1) is convex and that the curved surface (31) of articulation of the second plate (2) is concave.

Figure 1B:
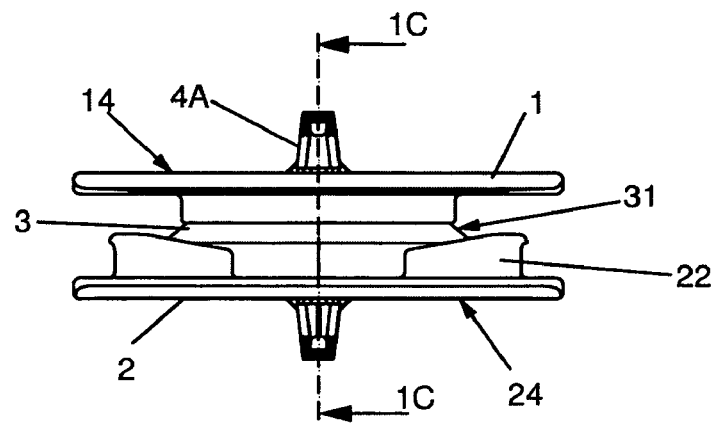
Figure 1C:
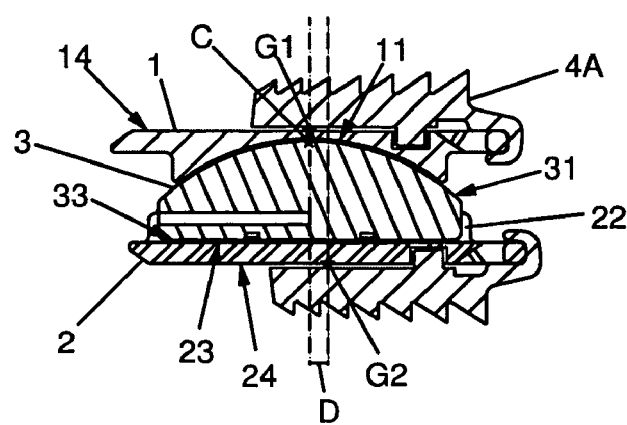
Figure 5A:
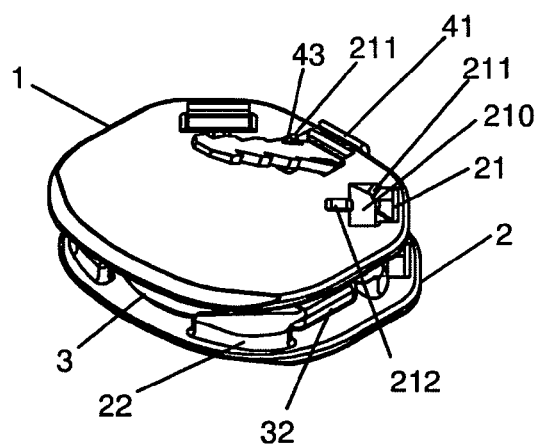
Figure 5B:
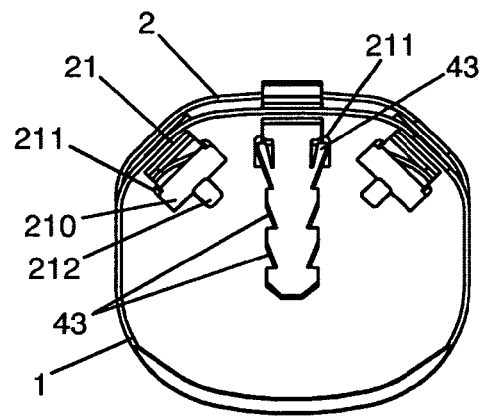
Figure 5C:
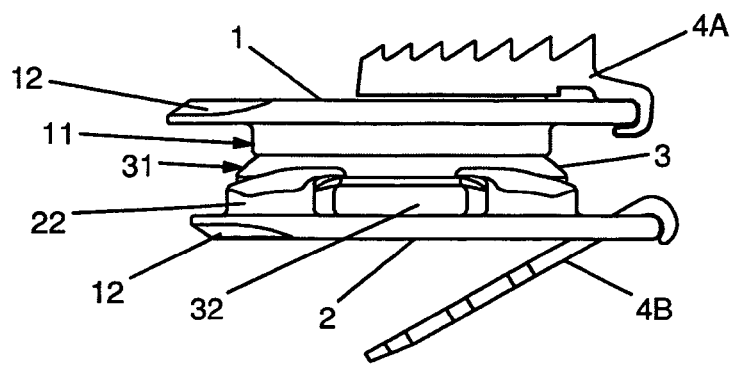

In the embodiment represented in FIGS. 1A to 1C, 3A, 3B and 5A to 5C, the prosthesis also comprises a core (3) comprising a plane surface (33) and a curved surface (31) of articulation. In the case of a prosthesis with three elements, only the first plate (1) comprises a curved surface of articulation (11) and this surface co-operates with at least a section of the curved surface (31) of the core (3) to which it is complementary, to allow to pivot and/or tilt the plates (1, 2) about each other. The plane surface (33) of the core (3) co-operates with at least a section of a plane surface (23) of the second plate (2) to allow a translation of the core (3) in relation to the second plate (2) in at least one direction perpendicular to the vertical axis of the spinal column and/or a rotation of the core (3) in relation to the second plate (2) via rotation about an axis substantially perpendicular to the plane of these plane surfaces. The second plate (2) comprises means for co-operating (22) which are complementary with means for co-operating (32) of the core (3) so as to restrict or abolish at least this translation of the core (3) in relation to the second plate (2). In the embodiments represented in figures, the means for co-operating (22) of the second plate (2) are female means located in the vicinity of the edges of the second plate (2) and co-operating with the male means (32) of the core (3). In the embodiments represented in the figures, these male means for co-operating (32) of the core (3) are two studs located on the two side edges of the core (3) and the female means for co-operating (22) of the second plate (2) are four walls located, in pairs, on each of the two side edges of the second plate (2). These walls comprise an inward curving section towards the centre of the plate (2) and partially covering the male means for co-operating (32) of the core (3) so as to prevent the core (3) from lifting. In another embodiment of the invention, the means for co-operating (22) of the second plate (2) can be male means located in the vicinity of the edges of the second plate (2) and co-operating with the female means (32) of the core (3). In an embodiment of the invention, the dimensions of each male means for co-operating (32, 22) can be slightly smaller than those of the female means for co-operating (22, 32) so as to allow a slight travel between the core (3) and the second plate (2) around the position corresponding to the vertical projection of the centre (C) of articulation. In another embodiment, the dimensions of each male means for co-operating (32, 22) can be substantially identical to those of each female means for co-operating (22, 32) so as to prevent any travel between the core (3) and the second plate (2) and to retain the core (3) in the position corresponding to the vertical projection of the centre (C) of articulation.

In this case of a prosthesis with three elements, the centre (C) of articulation is vertically aligned with the vertex of the curved surface (31) of articulation of the core (3) and correspond to the mid-position of the core (3) between the means for co-operating (22) of the second plate (2) and to the mid-position of the centre of the curved surface (11) of the first plate (1) in relation to the core (3). In the embodiment represented in the figures, the curved surface (11) of the first plate (1) is concave and the curved surface (31) of the core (3) is convex but it could be that the curved surface (11) of the first plate (1) is convex and that the curved surface (31) of the core (3) is concave.

In an embodiment of the invention, the centre (C) of articulation is vertically aligned with the centre (G1) of geometry of the first plate (1) but off-set in relation to the geometric centre (G2) of the second plate (2) in at least a direction perpendicular to the vertical axis of the spinal column. This off-setting (D) of the geometric centres (G1, G2) of the plates engenders an off-setting of the edges of the plates (1, 2) in at least one direction perpendicular to the vertical axis of the spinal column. In another embodiment of the invention, the centre (C) of articulation can also be off-set in relation to the geometric centre (G1) of the first plate (1). This off-setting of the centre (C) of articulation in relation to the geometric centre (G1) of the first plate (1) can be in the opposite direction to that of its off-setting (D) in relation to the geometric centre (G2) of the second plate (2) so that the vertical projection of the centre (C) of articulation lies between the vertical projections of the geometric centres (G1, G2) of the plates (1, 2) and so that the off-setting of the geometric centres (G1, G2) in relation to the centre (C) of articulation cumulate and engender an off-setting of the edges of the plates (1, 2) in at least one direction perpendicular to the vertical axis of the spinal column. This off-setting of the centre (C) of articulation in relation to the geometric centre (G1) of the first plate (1) can also be in the same direction as that of its off-setting (D) in relation to the geometric centre (G2) of the second plate (2), but at a lesser distance so that these off-settings partially compensate each other and engender an off-setting of the edges of the plates (1, 2) between themselves in at least one direction perpendicular to the vertical axis of the spinal column.

It can be beneficial that prostheses according to various embodiments of the invention allow correction of the slope defects of the adjacent vertebrae. The median planes representing the contact surfaces (14, 24) of the plates (1, 2) can therefore be substantially parallel or create an acute angle. The slope obtained by such an angle will allow the overall shape of the prosthesis to be adapted to the anatomy of the spinal column or to correct any possible slope defects of the vertebrae of the patient for whom the prosthesis is intended. The same plates (1, 2) are assembled with core (3) of different thicknesses and/or dimensions and/or shapes. The plates (1, 2) can comprise, at least on their anterior edge, at least a bevel (12) facilitating the insertion of the prosthesis between the vertebrae.

An embodiment of a prosthesis according to the invention comprises mobile osseous anchorage means (4A, 4B) allowing to anchor the plates (1, 2) in the vertebrae. These osseous anchorage means (4A, 4B) and/or the plates (1, 2) can thus comprise means for securing (43 and/or 211, 212) of the binding of the osseous anchorage means (4A, 4B) on the plates (1, 2).

In one embodiment of the mobile osseous anchorage means (4B), at least a plate (40), equipped with notches (42) oriented so as to prevent this notched plate (40) from falling out once inserted in a vertebra, is intended to be interlocked on to at least one edge (21) of an opening in the vicinity of the periphery of the plates (1, 2), thanks to an inwardly curved section (41). Thus, these mobile osseous anchorage means (4B) can be inserted into the vertebrae and interlocked on to the plates of the prosthesis once the latter has been inserted between the vertebrae. This embodiment of the mobile osseous anchorage means (4B) allows a possible adjustment of the position of the prosthesis between the vertebrae prior to definitive bonding. The end of the notched plate (40) opposite the one with an inwardly curved section (41) can comprise a bevel allowing to facilitate the insertion of the notched plate (40) into the vertebrae. The opening in the vicinity of the periphery of the plates (1, 2) can comprise a sloping section (210) on to which the notched plate (40) leans when the curved section (41) of the osseous anchorage means (4B) is interlocked on to the edge (21) of this opening. This sloping section (210) allows to set the angle of the osseous anchorage means (4B) in relation to the plates and to guide them when they are being inserted into the opening. The means for securing (43) can consist in flexible tabs (43) oriented towards the curved section (41) of the osseous anchorage means (4B) and intended to fold back against the edges of the plate (40) when inserting the osseous anchorage means (4B) into the openings in the plates (1, 2). During the interlocking of the curved sections (41) onto the edges (21) of the openings in the plates (1, 2), these flexible tabs (43) separate to lean against the limit stops (211) located on the walls of the openings in the plates (1, 2), so as to prevent the osseous anchorage means (4B) from falling out. In an alternative embodiment, the inwardly curved section (41) of the notched plate (40) of the mobile osseous anchorage means (4) extends via a second plate (40) also equipped with notches (42) oriented so as to prevent the plate (40) from falling out once inserted into the vertebrae.

In another embodiment the mobile osseous anchorage means (4A, 4B) of the plates (1, 2) at least one winglet (4A) is equipped with notches (42) oriented so as to prevent the winglet (4A) from falling out once inserted into a groove made in a vertebra. One end of the winglet (4A) has an inwardly curved section (41) and intended to be interlocked on to at least one edge (21) of an opening in the vicinity of the periphery of the plates (1, 2). The means for securing (43) of the winglet (4A) can thus consist in at least a stud (43) located on the lower surface of the winglet (4A) and intended to be interlocked into at least one hole (210) on the contact surfaces (14, 24) of the plates (1, 2). The stud (43) and the hole (210) will be of complementary shape and size so as to secure the winglet (4A) on to the plates (1, 2). In this embodiment, the vertebrae, between which the prosthesis is intended to be inserted, will have been previously prepared by the surgeon by hollowing out, in the vertebral plates, grooves of complementary shape and size with the shape and size of the winglets (4A).

It should be obvious for those skilled in the art that the invention allows embodiments under numerous other specific forms whilst remaining within the scope of the invention as claimed. Consequently, the embodiments should be considered as purely illustrative, but can be modified in the field defined by the impact of the attached claims, and the invention should not be restricted to the aforementioned details.

The invention claimed is:

1. Intervertebral disc prosthesis for implantation between vertebrae of a spinal column comprising at least a first plate and a second plate articulated about each other, with curved articulation surfaces providing articulation of at least one of the plates and allowing to pivot or tilt the plates in relation to each other via rotation about, respectively, an axis substantially perpendicular to the plane of one of the plates and an axis substantially in the plane of one of the plates, and a core comprising at least one core stop, a plane surface, and one of the curved articulation surfaces, which curved articulation surface of the core has a vertex, and the first plate comprises another of the curved articulation surfaces, which curved articulation surface of the first plate has a mid-position of its center in relation to the core;

the second plate comprises a plane surface, at least a portion of which co-operates with the plane surface of the core in order to allow a translation of the core in relation to the second plate in at least one direction perpendicular to the vertical axis of the spinal column and a rotation of the core in relation to the second plate at least about an axis perpendicular to the plane of the second plate;

at least one osseous anchor that is interlockable with at least one of the plates and that is movable independently of the plate prior to interlocking with the plate;

each of the plates comprises edges and a contact surface configured to be placed in contact with a vertebral plate of one of the vertebrae between which the prosthesis is intended to be implanted;

the contact surface for each of the plates comprises a geometric center at equal distance from at least two diametrically opposite points located on the periphery of the plate;

the geometric centers of each contact surface are off-set so that the plates are not vertically aligned; and the off-set of the geometrical centers of the contact surfaces off-sets the edges of the plates in at least one direction perpendicular to the vertical axis of the spinal column.

2. Intervertebral disc prosthesis according to claim 1, further comprising means for securing the binding of the osseous anchor on one of the first or the second plates.

3. Intervertebral disc prosthesis according to claim 2, in which the intervertebral disc prosthesis further comprises a center of articulation vertically aligned with the vertex of the curved articulation surface of the core and corresponding to the mid-position of the core in relation to a second plate stop and to the mid-position of the center of the curved articulation surface of the first plate.

4. Intervertebral disc prosthesis according to claim 3, in which the curved articulation surface of the first plate is concave and the curved articulation surface of the core is convex.

5. Intervertebral disc prosthesis according to claim 3, in which the core stop is male, and the second plate stop is female and located proximal to an edge of the second plate, said female second plate stop comprising at least one stop surface cooperating with said male core stop.

6. Intervertebral disc prosthesis according to claim 5, in which the female second plate stop comprises at least two stop surfaces and in which the dimensions of the male core stop is slightly smaller than the distance between the two stop surfaces of the female second plate stop in order to allow a slight travel between the core and the second plate around a position defined by a vertical projection along the axis of the spinal column of the center of articulation.

7. Intervertebral disc prosthesis according to claim 5 comprising two male core stops and two female second plate stops located proximal to each of the lateral edges of the second plate and each comprising at least two stop surfaces, in which the male core stops are two studs located on opposite lateral sides of the core and each cooperating with one female second plate stop.

8. Intervertebral disc prosthesis according to claim 7, in which the female second plate stops comprise a section dish-shaped towards the center of the plate and partly covering portions of the male core stops in order to prevent the core from lifting.

9. Intervertebral disc prosthesis according to claim 3, in which the first and second plates are configured to cooperate with a core that can have one or more thicknesses, dimensions, or shapes.

10. Intervertebral disc prosthesis according to claim 2, further comprising a vertex of the curved articulation surfaces and a center of articulation vertically aligned with the vertex of the curved articulation surfaces, said center of articulation being vertically aligned with the geometric center of the first plate but off-set in relation to the geometric center of the second plate in at least one direction perpendicular to the vertical axis of the spinal column.

11. Intervertebral disc prosthesis according to claim 2, in which a median plane represents the contact surfaces of each of the first and second plates, and said median planes are either substantially parallel or intersect to create an acute angle, the slope of said acute angle devised to adapt the intervertebral disc prosthesis to the spinal column or to correct one or more slope defects of the vertebrae of the spinal column.

12. Intervertebral disc prosthesis according to claim 2, in which each of the plates further comprises, at least on one edge, a bevel configured to facilitate the insertion of the prosthesis between the vertebrae.

13. Intervertebral disc prosthesis according to claim 2, in which the means for securing the binding of the winglet comprises at least one stud located on the lower surface of the winglet and configured to interlock into at least one hole in the contact surfaces of the plates, the stud and the hole being of complementary shape and size so as to secure the winglet in place on the plates.

14. Intervertebral disc prosthesis according to claim 1, in which
at least one of the first or second plates comprises an anchor opening located in the vicinity of the periphery of said plate and having at least one edge; and
the osseous anchor comprises a winglet having notches oriented to retain the winglet in a vertebra, one end of the winglet having a curved section that can be interlocked onto at least one edge of the anchor opening.

15. Intervertebral disc prosthesis according to claim 14, in which the intervertebral disc prosthesis further comprises a center of articulation vertically aligned with the vertex of the curved articulation surface of the core and corresponding to the mid-position of the core in relation to a second plate stop and to the mid-position of the center of the curved articulation surface of the first plate.

16. Intervertebral disc prosthesis according to claim 15, in which the curved articulation surface of the first plate is concave and the curved articulation surface of the core is convex.

17. Intervertebral disc prosthesis according to claim 15, in which the core stop is male, and the second plate stop is female and located proximal to an edge of the second plate, said female second plate stop comprising at least one stop surface cooperating with said male core stop.

18. Intervertebral disc prosthesis according to claim 17, in which the female second plate stop comprises at least two stop surfaces and in which the dimensions of the male core stop is slightly smaller than the distance between the two stop surfaces of the female second plate stop in order to allow a slight travel between the core and the second plate around a position defined by a vertical projection along the axis of the spinal column of the center of articulation.

19. Intervertebral disc prosthesis according to claim 17 comprising two male core stops and two female second plate stops located proximal to each of the lateral edges of the second plate and each comprising at least two stop surfaces, in which the male core stops are two studs located on opposite lateral sides of the core and each cooperating with one female second plate stop.

20. Intervertebral disc prosthesis according to claim 19, in which the female second plate stops comprise a section dish-shaped towards the center of the plate and partly covering portions of the male core stops in order to prevent the core from lifting.

21. Intervertebral disc prosthesis according to claim 15, in which the first and second plates are configured to cooperate with a core that can have one or more thicknesses, dimensions, or shapes.

22. Intervertebral disc prosthesis according to claim 14, further comprising a vertex of the curved articulation surfaces and a center of articulation vertically aligned with the vertex of the curved articulation surfaces, said center of articulation being vertically aligned with the geometric center of the first plate but off-set in relation to the geometric center of the second plate in at least one direction perpendicular to the vertical axis of the spinal column.

23. Intervertebral disc prosthesis according to claim 14, in which a median plane represents the contact surfaces of each of the first and second plates, and said median planes are either substantially parallel or intersect to create an acute angle, the slope of said acute angle devised to adapt the intervertebral disc prosthesis to the spinal column or to correct one or more slope defects of the vertebrae of the spinal column.

24. Intervertebral disc prosthesis according to claim 14, in which each of the plates further comprises, at least on one edge, a bevel configured to facilitate the insertion of the prosthesis between the vertebrae.

* * * * *